US007929662B2

(12) United States Patent
Warner et al.

(10) Patent No.: US 7,929,662 B2
(45) Date of Patent: Apr. 19, 2011

(54) FLOW METHOD AND APPARATUS FOR SCREENING CHEMICALS USING MICRO X-RAY FLUORESCENCE

(75) Inventors: Benjamin P. Warner, Los Alamos, NM (US); George J. Havrilla, Los Alamos, NM (US); Thomasin C. Miller, Bartlesville, OK (US); Cris Lewis, Los Alamos, NM (US); Cynthia A. Mahan, Los Alamos, NM (US); Cyndi A. Wells, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 12/396,592

(22) Filed: Mar. 3, 2009

(65) Prior Publication Data

US 2009/0175410 A1    Jul. 9, 2009

Related U.S. Application Data

(63) Continuation of application No. 11/444,660, filed on May 31, 2006, now Pat. No. 7,519,145, which is a continuation-in-part of application No. 11/125,036, filed on May 9, 2005, now abandoned, which is a continuation of application No. 10/206,524, filed on Jul. 25, 2002, now abandoned.

(51) Int. Cl.
*G01N 23/223*    (2006.01)
(52) U.S. Cl. ........................................................ 378/47
(58) Field of Classification Search ................. 378/44, 378/45, 47
See application file for complete search history.

(56) References Cited

U.S. PATENT DOCUMENTS

| | | | |
|---|---|---|---|
| 4,745,285 A | 5/1988 | Recktenwald et al. |
| 5,482,867 A | 1/1996 | Barrett et al. |
| 5,574,284 A | 11/1996 | Farr |
| 5,660,703 A | 8/1997 | Dasgupta |
| 5,668,373 A | 9/1997 | Robbat et al. |
| 5,778,039 A | 7/1998 | Hossain et al. |
| 5,982,847 A | 11/1999 | Nelson |
| 6,027,890 A | 2/2000 | Ness et al. |
| 6,147,344 A | 11/2000 | Annis et al. |
| 6,207,861 B1 | 3/2001 | Nash et al. |
| 6,225,132 B1 | 5/2001 | Drukier et al. |
| 6,344,334 B1 | 2/2002 | Ellman et al. |
| 6,395,169 B1 | 5/2002 | Hindsgaul et al. |

(Continued)

OTHER PUBLICATIONS

Office of Science and Technology of the Center for Devices and Radiological Health of the U.S. Food and Drug Administration, "Annual Report—Fiscal Year 1995", published online Aug. 8, 1996 at the web site http://www.fda.gov/cdrh/ost/reports/fy95/index.html, chapter entitled "Diagnostic Imaging" at the website http://www.fda.gov/cdrh/ost/reports/fy95/diagnostic_imaging.html.

(Continued)

*Primary Examiner* — Chih-Cheng G Kao
(74) *Attorney, Agent, or Firm* — Husch Blackwell LLP

(57) ABSTRACT

Method and apparatus for screening chemicals using micro x-ray fluorescence. A method for screening a mixture of potential pharmaceutical chemicals for binding to at least one target binder involves flow separating a solution of chemicals and target binders into separated components, exposing them to an x-ray excitation beam, detecting x-ray fluorescence signals from the components, and determining from the signals whether or not a binding event between a chemical and target binder has occurred.

10 Claims, 5 Drawing Sheets

U.S. PATENT DOCUMENTS

| | | |
|---|---|---|
| 6,496,562 B1 | 12/2002 | Henrich et al. |
| 6,697,454 B1 | 2/2004 | Nicolich et al. |
| 7,519,145 B2 * | 4/2009 | Warner et al. .................. 378/47 |

OTHER PUBLICATIONS

Stephanie M. Mann et al., "Element-Specific Detection in Capillary Electrophoresis Using X-ray Fluorescence Spectroscopy," Analytical Chemistry, vol. 72, No. 8, pp. 1754-1758, Apr. 15, 2000.

Finny G. Kuruvilla et al., "Dissecting Glucose Signalling with Diversity-Oriented Synthesis and Small-Molecule Microarrays," Nature, vol. 416, Apr. 11, 2002, pp. 653-657.

Bruce Alberts et al,. "Molecular Biology of the Cell," Second Edition, Garland Publishing, Inc. 1989, pp. 159-160.

Arnold J. Gordon et al., "The Chemist Companion," John Wiley & Sons, 1972, pp. 369-370.

Bruce Scruggs, "XRF Elemental Analyzers," MRS Bulletin, vol. 24, No. 11, Nov. 1999, p. 1.

* cited by examiner

FLOW METHOD AND APPARATUS FOR SCREENING CHEMICALS USING MICRO X-RAY FLUORESCENCE

RELATED APPLICATIONS

This application is a continuation of co-pending U.S. patent application Ser. No. 11/444,660 filed May 31, 2006, which is a continuation-in-part of U.S. patent application Ser. No. 11/125,036 filed May 9, 2005, now abandoned, which is a continuation of U.S. patent application Ser. No. 10/206,524 filed Jul. 25, 2002, now abandoned, all hereby incorporated by reference.

STATEMENT REGARDING FEDERAL RIGHTS

This invention was made with government support under contract number W-7405-ENG- 36 and its successor contract number DE-AC52-06NA25396 awarded by the U.S. Department of Energy. The government has certain rights in the invention.

BACKGROUND OF THE INVENTION

The present invention relates generally to detecting binding events and more particularly to a flow method for detecting binding events between a potential pharmaceutical chemical and a target binder using micro-x-ray fluorescence spectroscopy.

Pharmaceutical chemicals are the active ingredients in drugs such as the now popular Prilosec™, Lipitor™, Zocor™, Prozac™, Zoloft™, and Celebrex™, and it is believed that their pharmaceutical properties are linked to their ability to bind to the "binding site" of one or more proteins. The binding properties of a protein largely depend on the exposed surface amino acid residues of the polypeptide chain (see, for example, Bruce Alberts et al., "Molecular Biology of the Cell', 2nd edition, Garland Publishing, Inc., New York, 1989; and H. Lodish et al., "Molecular Cell Biology", 4th edition, W. H. Freeman and Company, 2000). These amino acid residues can form weak noncovalent bonds with ions and other molecules. Effective binding generally requires the formation of many weak bonds at the "binding site" of the protein. The binding site is usually a cavity in the protein formed by a specific arrangement of amino acids. There must be a precise fit with the binding site for effective binding to occur. The shapes of binding sites may differ greatly among different proteins, and even among different conformations of the same protein. Even slightly different conformations of the same protein may differ greatly in their binding abilities. For these reasons, it is extremely difficult to predict which chemicals will bind effectively to proteins.

It can take many years to identify an effective pharmaceutical chemical. The desire to hasten the identification of important pharmaceutical chemicals is a constant challenge that has prompted the use or screening strategies for screening a large number of structurally or chemically related materials, known in the art as a "library", for binding properties to proteins.

Screening methods generally involve combining potential pharmaceutical chemicals with target binders and determining which, if any, of the potential pharmaceutical chemicals bind to any of the target binders. Potential pharmaceutical chemicals are preferably water-soluble organic compounds that can dissolve into the blood stream. Target binders are generally biological materials such as enzymes, non-enzyme proteins, DNA, RNA, microorganisms (e.g. prions, viruses, bacteria, and the like), human cells, plant cells, animal cells, and the like. Potential pharmaceutical chemicals that bind to at least one target binder are likely candidates for further investigation of pharmaceutical properties (e.g. efficacy and toxicity).

Some of the known screening methods are described in the following three patents.

U.S. Pat. No. 6,147,344 to D. Allen Annis et al. entitled "Method for Identifying Compounds in a Chemical Mixture", which issued Nov. 14, 2000, describe a method for automatically analyzing mass spectrographic data from mixtures of chemical compounds.

U.S. Pat. No. 6,344,334 to Jonathan A. Ellman et al. entitled "Pharmacophore Recombination for the Identification of Small Molecule Drug Lead Compounds", which issued Feb. 5, 2002, describes a method for identifying a drug lead compound that inhibits binding of target biological molecules by contacting these target biological molecules with a library of cross-linked, target, binding fragments.

U.S. Pat. No. 6,395,169 to Ole Hindsgaul et al. entitled "Apparatus for Screening Compound Libraries", which issued May 28, 2002, describes an apparatus that employs frontal chromatography combined with mass spectometry to identify and rank members of a library that bind to target receptor.

Screening methods sometimes employ tagged materials because the analogous untagged material is otherwise not visible using the analytical technique chosen for the screening method. Tagging may involve attaching a labeled chemical portion to a chemical. An example of a screening method requiring tags is fluorescence activated cell sorting. An example of this method involves preparing a solution of cells and antibodies bearing a fluorescent tag. Some of the antibodies bind to some of the cells. One at a time, the cells flow past a laser beam and a detector (such as a ultraviolet/visible fluorescence detector). Cells that fluoresce (are bound to the tagged antibodies) and are then deflected into a collector (see, for example, Bruce Alberts et al., "Molecular Biology of the Cell", 2nd edition, Garland Publishing, Inc., New York, 1989, pages 159-160).

It is generally assumed that the attachment of a fluorescent tag only serves to make visible the otherwise invisible chemical and/or target binder, and does not alter the binding properties of the untagged analog. Since it is well known that even small changes to the structure of a chemical or target binder may affect its function, this assumption may not be a valid one. Tagged surrogates are structurally different from their untagged counterparts, and these structural differences could affect their binding properties.

An efficient method for screening potential pharmaceutical chemicals for binding to target binders remains highly desirable.

SUMMARY OF THE INVENTION

In accordance with the objects and purposes of the present invention, as embodied and broadly described herein, the present invention includes a method for determining whether or not chemical binding occurs between at least one target binder and at least one chemical to form a bound complex. The method includes preparing a solution comprising at least one chemical and at least one target binder; flow-separating the solution into at least two separated components; exciting atoms of the chemical and of a chemical portion of any bound complex present in any flow separated component with a polychromatic x-ray excitation beam in order to produce an x-ray fluorescence signal therefrom; detecting the x-ray fluorescence signal produced from the excited atoms present in the chemical and the chemical portion of any bound complex present in a separated component; and determining from the x-ray fluorescence signal produced from the excited atoms present in the chemical and the chemical portion of any bound complex present in a separated component whether or not any separated component comprises a bound complex.

The invention also includes a method for determining whether or not chemical binding occurs between at least one target binder and at least one chemical to form a bound complex. The method includes preparing a solution comprising at least one chemical and at least one target binder; flow separating the solution into at least two separated components; exciting atoms of the chemical and of a chemical portion of any bound complex present in any flow-separated component using an x-ray excitation beam comprising x-rays of less than 9 KeV in order to produce an x-ray fluorescence signal therefrom; detecting the x-ray fluorescence signal produced from the excited atoms present in the chemical and in the chemical portion of any bound complex present in a separated component; and determining from the x-ray fluorescence signal produced from the excited atoms present in the chemical and the chemical portion of any bound complex present in a separated component whether or not any separated component comprises a bound complex.

The invention also includes method for determining whether or not chemical binding occurs between at least one target binder and at least one chemical to form a bound complex. The method involves preparing a solution comprising at least one chemical and at least one target binder; flow-separating the solution using a pressure gradient into at least two separated components; exciting atoms of a chemical and of a chemical portion of any bound complex present in any flow-separated component using an x-ray excitation beam to produce an x-ray fluorescence signal therefrom; detecting the x-ray fluorescence signal produced from the excited atoms present in the chemical and the chemical portion of any bound complex present in a separated component; and determining from the x-ray fluorescence signal produced from the excited atoms present in the chemical portion of any bound complex present in a separated component whether or not any separated component comprises a bound complex.

The invention also includes an apparatus for screening chemical binding. The apparatus includes a flow separator for separating a solution of chemicals and at least one target binder into at least two flow-separated components; an x-ray excitation source for exposing at least one of said flow-separated components to an x-ray excitation beam to produce an x-ray fluorescence signal therefrom; an x-ray detector for detecting the x-ray fluorescence signal emitted from a flow-separated component; and a pump engaged with said flow separator for providing a pressure gradient along said flow separator.

The invention also includes an apparatus for screening chemical binding. The apparatus includes a flow separator for separating a solution into at least two flow separated components, the solution comprising at least one chemical and at least one target binder; a polychromatic x-ray excitation source for exposing at least one of the flow-separated components to an x-ray excitation beam to produce an x-ray fluorescence signal therefrom; and an x-ray detector for detecting the x-ray fluorescence signal emitted from a flow-separated component.

The invention also includes an apparatus for screening chemical binding. The apparatus includes a flow separator for separating a solution of chemicals and at least one target binder into at least two flow-separated components; an x-ray excitation source for exposing at least one of said flow-separated components to an x-ray excitation beam comprising x-rays of less than 9 KeV to produce an x-ray fluorescence signal therefrom; and an x-ray detector for detecting the x-ray fluorescence signal emitted from a flow-separated component.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION OF THE INVENTION

Figure 1A:
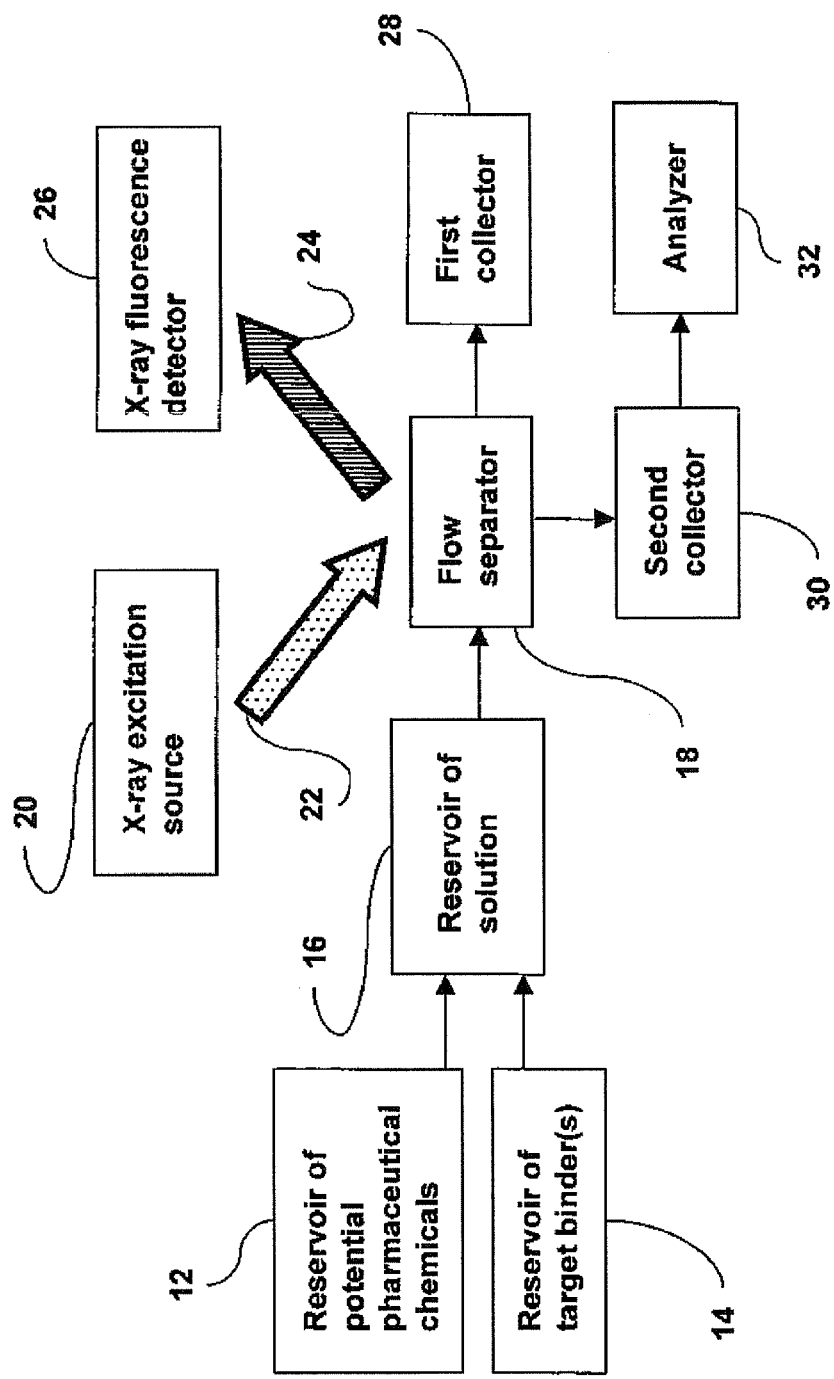
FIGS. 1a-b show typical process flow diagrams for the invention.

Briefly, the present invention includes a method for identifying binding events between potential pharmaceutical chemicals and target binders. The method involves modifying a mixture of potential pharmaceutical chemicals by adding at least one target binder to the mixture. After allowing sufficient time for any bound complex between any of the potential pharmaceutical chemicals and any of the target binders to form, if such a complex can form, the resulting solution is flow separated into at least two components. Each component is exposed to an x-ray excitation beam. If the exposed component emits a detectable x-ray fluorescence signal, that component is isolated. The identity of any isolated component can be determined using one or more standard analytical techniques, such as gas chromatography, liquid chromatography, mass spectrometry, nuclear magnetic resonance spectroscopy, infrared spectroscopy, ultraviolet spectroscopy, visible spectroscopy, elemental analysis, cell culturing, immunoassaying, and the like.

The method of the invention uses x-ray fluorescence as a probe to detect binding events. X-ray fluorescence is a powerful technique that has been used to determine the chemical elements that are present in a chemical sample, and to determine the quantity of those elements in the sample. The underlying physical principal of the method is that when an atom of a particular element is irradiated with x-ray radiation, the atom ejects a core electron such as a K shell electron. The resulting atom is in an excited state, and it can return to the ground state by replacing the ejected electron with an electron from a higher energy orbital. This is accompanied by the emission of a photon, i.e. x-ray fluorescence, and the photon energy is equal to the difference in the energies of the two electrons. Each element has a characteristic set of orbital energies and therefore, a characteristic x-ray fluorescence spectrum.

Many popular pharmaceutical chemicals, such as Prilosec™, Lipitor™, Zocor™, Prozac™, Zoloft™, and Celebrex™, contain the elements fluorine, chlorine, and/or sulfur. X-ray fluorescence is especially suited for detecting potential pharmaceutical chemicals because it can be used to detect and quantify these elements, and in general, to detect and quantify any element with an atomic number of nine or higher.

The invention also includes an apparatus for screening a mixture of potential pharmaceutical chemicals for binding to at least one target binder. The apparatus includes a container for containing a solution of a mixture of chemicals and at least one target binder. The apparatus also includes a flow separator for separating the solution into at least two separated components. The apparatus also includes an x-ray excitation source for exposing at least one of the flow-separated components to an x-ray excitation beam. The apparatus also includes an x-ray detector for detecting an x-ray fluorescent signal emitted from a flow-separated component, a diverter for diverting a chosen flow-separated component, and a container for isolating the chosen, flow-separated component.

An x-ray fluorescence spectrometer includes an x-ray excitation source and an x-ray detector. It is capable of irradiating a sample with an x-ray beam, detecting the x-ray fluorescence from the sample, and using the x-ray fluorescence to determine which elements are present in the sample and providing the quantity of these elements. The x-ray fluorescence spectrometer used to demonstrate the invention was the commercially available EDAX Eagle XPL energy dispersive x-ray fluorescence spectrometer, equipped with a microfocus x-ray tube, lithium drifted silicon solid-state detector, processing electronics, and vendor supplied operating software.

The use of capillary electrophoresis with x-ray fluorescence has been described by Mann et al. in "Element Specific Detection in Capillary Electrophoresis Using X-Ray Fluorescence Spectroscopy", Analytical Chemistry, vol. 72, pp. 1754-1758, (2000), incorporated by reference herein. Mann et al. report the preparation of a mixture of chelation complexes of CDTA (cyclohexane diamine tetraacetic acid) and subsequent separation using capillary electrophoresis. The separated complexes were detected using a synchrotron-generated monochromatic, 10 keV x-ray beam.

Figure 1B:
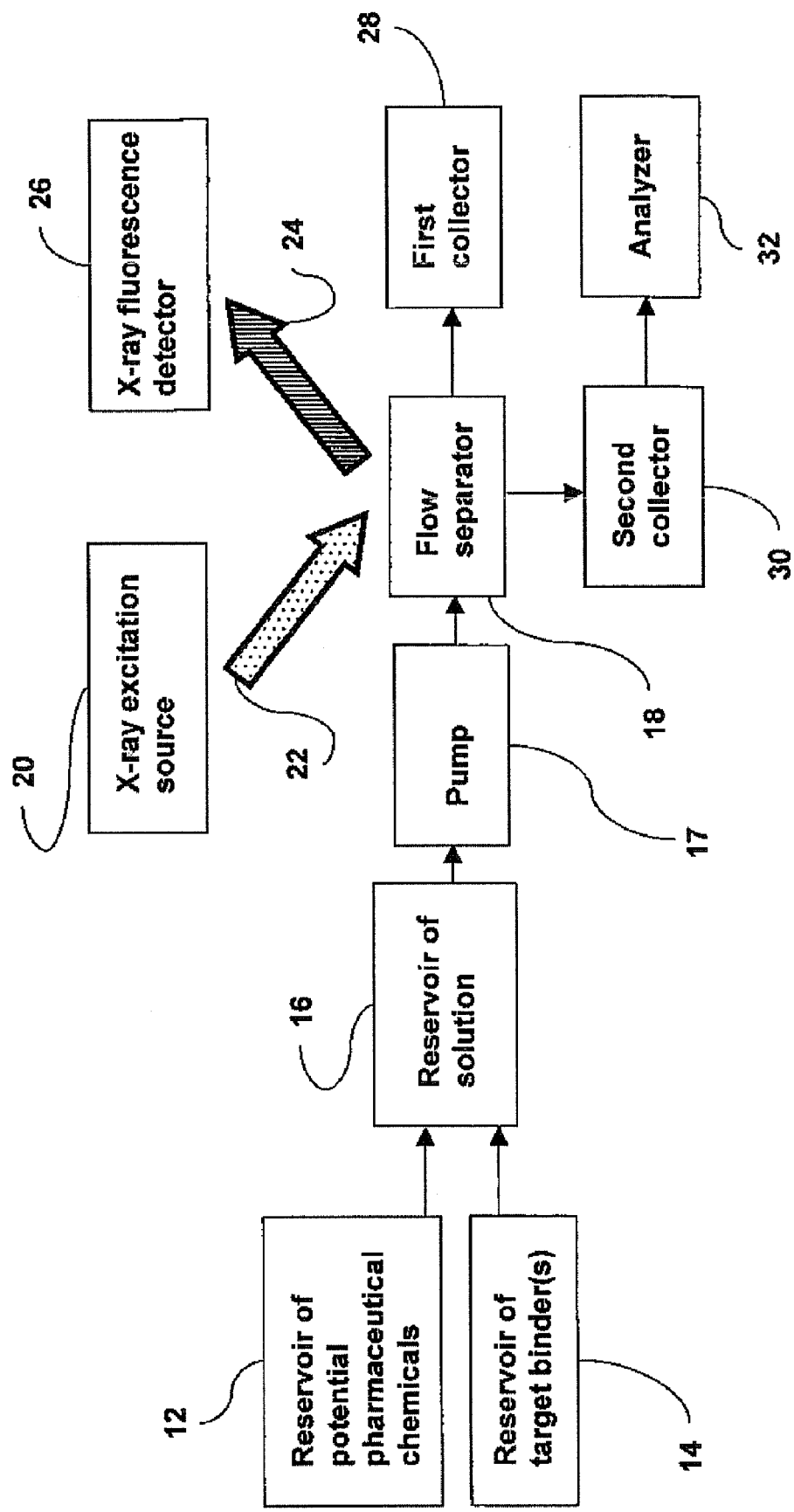

The practice of the invention can be further understood with the accompanying figures. Similar or identical structure is identified using identical callouts. FIGS. 1a-b show typical process flow diagrams for the invention. According to the invention, potential pharmaceutical chemicals from optional reservoir 12 are combined with at least one target binder from target binder reservoir 14 to form a solution in reservoir 16. Potential pharmaceutical chemicals used with the invention are typically water soluble organic chemicals, and have at least one element with an atomic number of nine or greater. Preferably, they include at least one element selected from fluorine, chlorine, bromine, iodine, sulfur, phosphorus, selenium, lanthanum, cerium, praseodymium, neodymium, samarium, europium, gadolinium, terbium, dysprosium, holmium, erbium, thulium, ytterbium, lutetium, antimony, bismuth, and arsenic. Target binders that can be used with the invention include enzymes, non-enzyme proteins, DNA, RNA, plant cells, animal cells, human cells, and microorganisms (e.g. comprise prions, viruses, bacteria) and the like.

The solution of the mixture of potential pharmaceutical chemicals and target binder(s) enters flow separator 18 (see FIG. 1a), or first enters pump 17 and then flow separator 18 (see FIG. 1b). Flow separator 18 uses a mobile phase to flow separate the solution into at least two components. The target binder and chemical may be introduced into the flow separator at different times and/or at different locations along the flow separator. Flow separators that can be used with the invention include, but are not limited to, centrifuges, cell sorters, or chromatographs (e.g. liquid chromatograph such as high performance liquid chromatographs and fast protein listed chromatographs; electrophoretic separators such as capillary electrophoretic separators, gel filtration chromatographs, gel permeation chromatographs, size exclusion filters, dialysis filters, and the like). Preferably, the separator is a capillary electrophoresis separator, i.e. a long thin tube with a mobile phase (e.g. an aqueous buffer solution) inside the tube, and an electric potential across the length of the tube.

As the mixture separates into components, they are exposed to x-rays. After x-ray excitation source 20, preferably a rhodium target x-ray tube, delivers a polychromatic x-ray beam 22 to a separated component, that component may or may not emit an x-ray fluorescence signal 24, which is detected by x-ray fluorescence detector 26, x-ray detectors that can be used with the invention include, but at not limited to, lithium-drifted silicon detectors, silicon drift detectors, or PIN diodes. If the exposed component does not emit an x-ray fluorescence signal, that component is directed to first collector 28. If the exposed component emits a fluorescence signal that is detected by x-ray fluorescence detector 26, it is directed to second collector 30. This component is expected to include at least one bound complex of potential pharmaceutical chemical and target binder.

Figure 2:
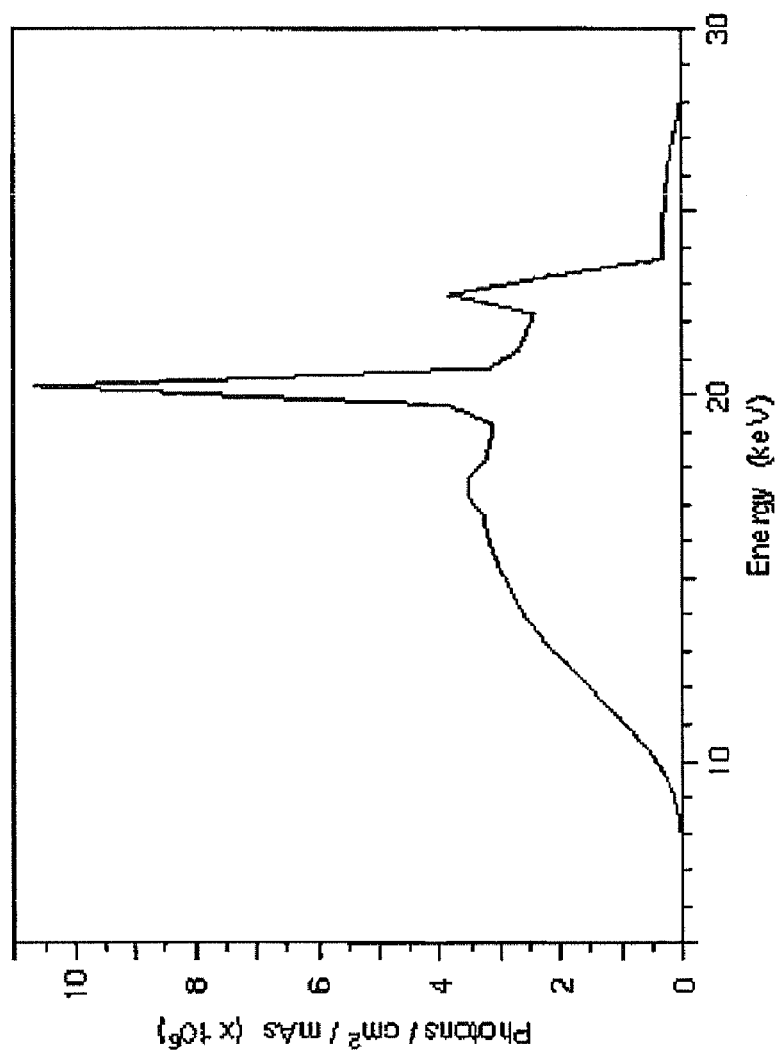
FIG. 2 shows a spectrum of polychromatic light produced using a Rhodium target excitation source.

A polychromatic x-ray excitation source (a rhodium source, for example) useful with the invention preferably provides x-rays having energies less than about 9 KeV, and more preferably less than about 8 KeV. The polychromatic source preferably also provides x-rays having energies greater than about 12 KeV. FIG. 2 shows an energy spectrum of an exemplary Rhodium source, which provides polychromatic x-rays having energies less than 9 KeV and greater than 12 KeV. It should be understood that other target x-ray excitation sources besides Rh could also be used.

While only a first collector and a second collector are shown in FIGS. 1a-b, it should be understood that more collectors may be used, depending on the number of separated components that are isolated from the mixture. In another embodiment of the invention, no collectors are used.

The separated component that emits a detectable x-ray fluorescence signal, i.e. the component directed to second collector 30, may then be sent to analyzer 32. Analyzers that can be used with the invention include, but are not limited to, gas chromatographs, liquid chromatographs, mass spectrometers, nuclear magnetic resonance spectrometers, infrared spectrometers, ultraviolet-visible (UV-VIS) spectrometers, fluorimeters, combustion analyzers (for elemental analysis), cell cultures, immunoassays, and the like. The choice of analyzer will depend on the nature of the potential pharmaceutical chemicals and/or binders being analyzed.

Figure 3:
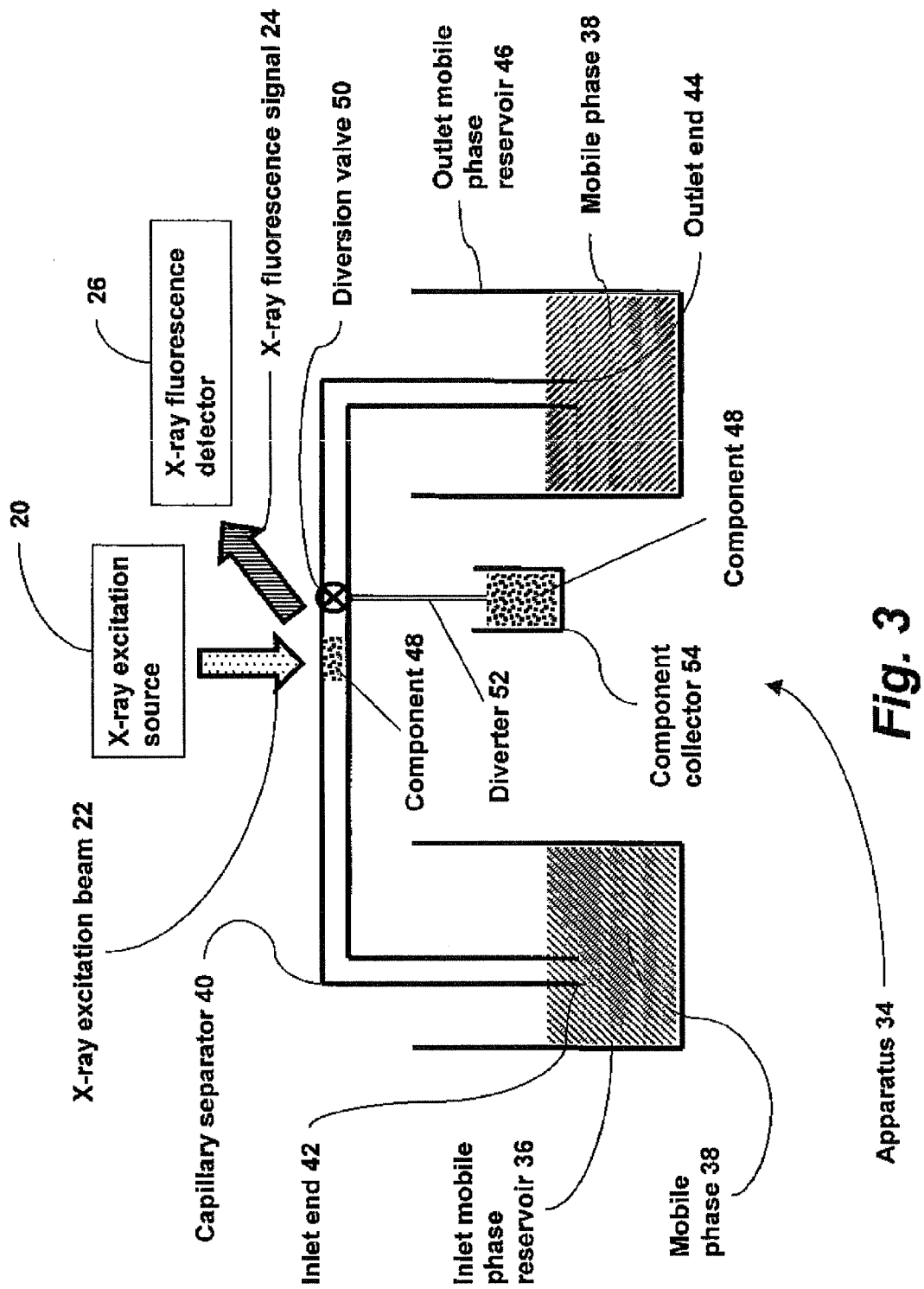
FIG. 3 shows a schematic representation of an embodiment apparatus of the invention.

FIG. 3 shows a schematic view of an embodiment of a screening apparatus of the invention. As FIG. 3 shows, screening apparatus 34 includes inlet mobile phase reservoir 36, which provides the mobile phase 38 for capillary separator 40. Inlet end 42 of separator resides in inlet mobile phase reservoir 36, while outlet and 44 resides in outlet mobile phase reservoir 46. After mobile phase 38 fills separator 40, an amount of a mixture of potential pharmaceutical chemicals and at least one target binder is introduced into inlet end 42 of separator 40. Inlet end 42 is then replaced into mobile phase reservoir 36. An electric potential between inlet end 42 and outlet end 44 of separator 40 drives the flow of the mobile phase 38 and of the mixture through separator 40. As FIG. 3 shows, component 48 has separated from the mixture. FIG. 3 also shows x-ray excitation source 20 directing x-ray excitation beam 22 at separated component 48, which then emits x-ray fluorescence signal 24 that is detected by x-ray fluorescence detector 26. The detection of an emitted x-ray fluorescence signal triggers diversion valve 50, which diverts the flow of mobile phase 36 and separated component 48 to diverter 52, which directs mobile phase 36 and separated component 48 to component collector 54.

The separation previously described was achieved using an electric potential, which provided an electric gradient across the length of capillary separator 40. The separation can also be achieved by applying a pressure gradient along the length of the tub. In this embodiment, the tube would include a stationary phase; a sample injection inlet would be used to introduce the solution into the tube, and a pump would provide the pressure gradient, as it does for high performance liquid chromatography.

As FIG. 3 shows component 48 is separated along a horizontal portion of capillary separator 40. This particular configuration is likely not optimal for separating complexes derived from using microorganism or cell target binders. For these target binders, a separator/sorter that separates along a vertical portion is preferred.

Figure 4:
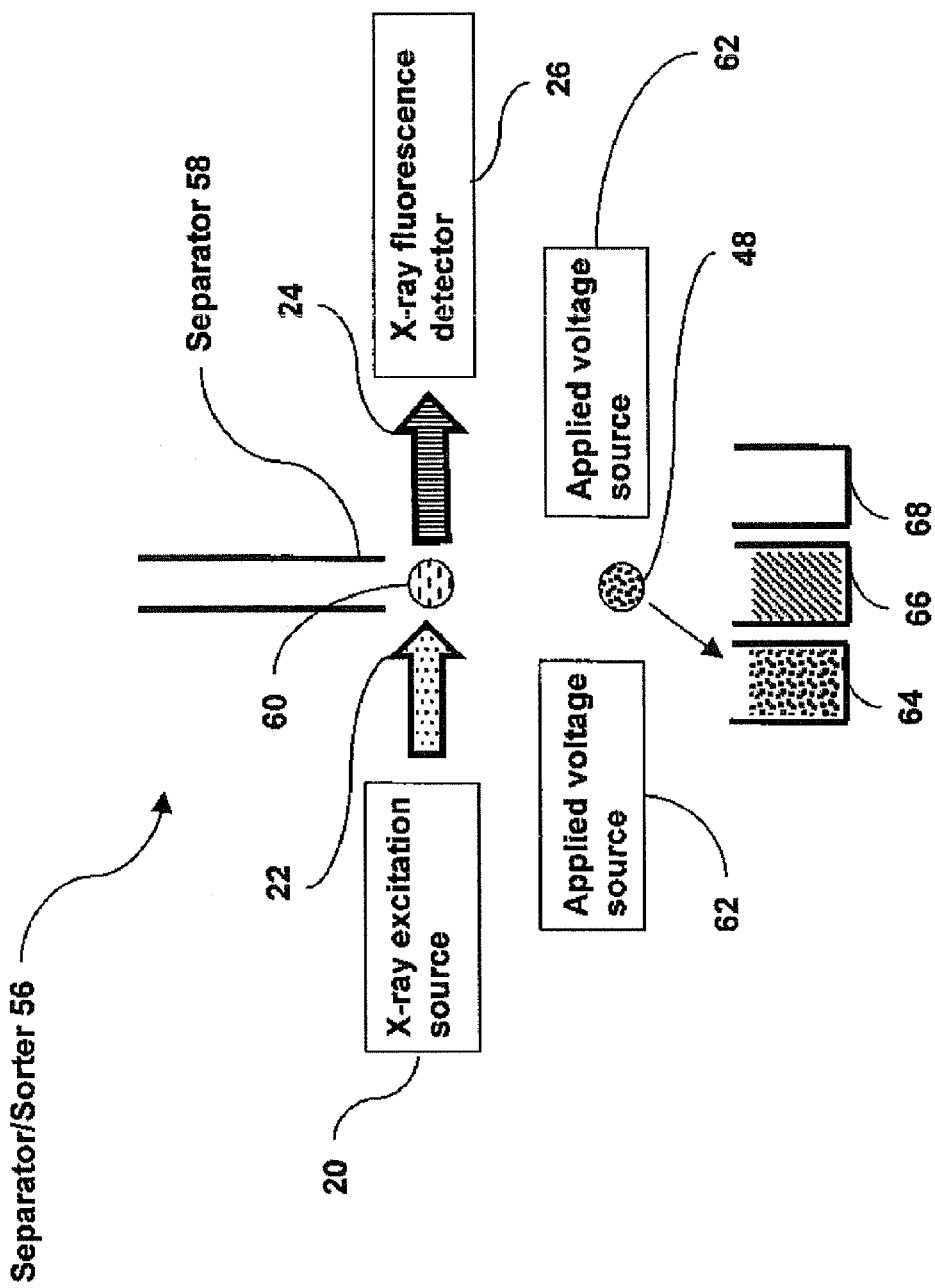
FIG. 4 shows an embodiment separator/sorter for sorting flow-separated components of a solution.

FIG. 4 shows an embodiment of such a separator/sorter that can be used with the invention. Separator/sorter 56 can be used for separating and sorting mixtures derived from cells, microorganisms, microspheres having attached proteins or nucleic acids, and the like. Separator/sorter 56 includes vertical separator 58 through which separation occurs. As FIG. 4 shows, the mixture has been separated into component 48 and component 60. Component 48 is had been subjected to x-ray beam 22 from x-ray excitation source 20 has emitted an x-ray fluorescence signal, which was detected by x-ray fluorescence detector 26. This triggered a response in applied voltage course 62, which applies a voltage that deflects component 48 into collector 64. If component 60 does not emit a detectable x-ray fluorescence signal, no voltage will be applied to deflect component 60 and it will flow into collector 66. However, if component 60 emits a detectable x-ray fluorescence signal, a voltage will be applied to deflect component 60 and it will flow into collector 68.

Separator/sorter 56 may include a laser source and associated detectors for performing conventional fluorescence activated cell sorting of the type described by Bruce Alberts et al., "Molecular Biology of the Cell", 2nd edition, Garland Publishing, Inc., New York, 1989, pages 159-160.

If a pharmaceutical chemical is needed to bond to a specific target binder protein, for example, a large number of different potential pharmaceutical chemicals can be screened according to the invention for binding to that protein. The invention can be used to distinguish which of the potential pharmaceutical chemicals bind strongly to the protein from those that bind weakly or not at all. The protein would be combined with about 10 to 10,000 potential pharmaceutical chemicals, wherein each of the potential pharmaceutical chemicals includes at least one element having an atomic number of nine or higher. Preferably, the potential pharmaceutical chemicals include an element having an atomic number of nine or higher that is not found in the target binder to simplify the screening method.

The invention could be used to, for example, determine whether either cobalt ion ($Co^{2+}$) and/or cyanocobalamin bind to the known, biologically active protein Ure2p (see Kuruvilla et al., "Dissecting Glucose Signaling With Diversity-Oriented Synthesis and Small-Molecule Microarrays", Nature, Vol. 416, pp. 653-657). An aqueous solution of cobalt (II) nitrate and cyanocobalamin would be added to Ure2p. The resulting aqueous solution would be flow separated according to the invention using, for example, a capillary electrophoresis separator. Any complex formed between the Ure2p and $Co^{2+}$ and/or cyanocobalamin should have a retention time that differs from either $Co^{2+}$ or cyanocobalamin, would emit a detectable x-ray fluorescence signal, and would be isolable using the invention.

The separation could be performed using, for example, a fused silica capillary tube (POLYMICRO TECHNOLOGIES™) having the following dimensions: 70 cm in length, 100 μm outer diameter (od), and a BERTAN™ Model ARB-30 high voltage power supply to provide the electric potential. The tube could be conditioned by first flushing it with a 1.0 molar (M) solution of NaOH for 15 min, then rinsing with distilled, de-ionized water for 15 min, and then flushing and filling with 75 mM Trisma run buffer (pH 8.0) for an additional 15 min.

A baseline was obtained by introducing an aqueous mixture of cobalt nitrate ($Co(NO_3)_2$, and cyanocobalamin (10.2 mM) into the capillary tube, applying a potential of 10 kV between the ends of the tube, and separating the mixture into its components. An EDAX™ Eagle II micro x-ray fluorescence system equipped with a Rh target excitation source and a SiLi detector was used to interrogate each separated component and measure any emitted x-ray fluorescence signal. The x-ray tube of the system was operated at 40 kV and 1000 μ. The $CoK_\alpha$ x-ray emission was monitored to detect unbound $Co^{2+}$ and cyanocobalamin. The spectrum acquisition time was about 10 seconds (s). The peak due to unbound $Co^{2+}$ was detected at about 4.5 min with a full-width-at-half-maximum (FWHM) of about 1 min. The cyanocobalamin peak was detected at about 8.5 min with a FWHM of about 1.5 min.

Similarly, the invention could be used to determine whether ferritin and/or cyanocobalamin bind to Ure2. An aqueous solution of ferritin and cyanocobalamin would be added to Ure2. The resulting aqueous solution could be flow separated using a capillary electrophoresis separator. When exposed to an x-ray beam, the iron in ferritin and the cobalt in cyanocobalamin each emit distinct and detectable x-ray fluorescence signals that could be used to determine whether a complex between ferritin and/or cyanocobalamin and Ure2p is formed.

A baseline was obtained as follows: A capillary electrophoresis separator was prepared using a Bertan™ Model ARB-30 high voltage power supply to provide the separation potential and a fused silica capillary tube (Polymicro Technologies™) having the following dimensions: 70 cm in length, 100 μm inner diameter (id), 170 μm outer diameter (od). The tube was conditioned by first flushing it with a 1.0 molar (M) solution of NaOH for 15 min, then rinsing with distilled, de-ionized water for 15 min, and then flushing with 100 mM Trisma run buffer (pH 8.0) for an additional 15 min.

An aqueous solution of ferritin (1.16 mg/ml) and cobalamin (10.2 mM) was introduced into the capillary tube. After a separation potential of 9.5 kV was applied between the ends of the tube, the solution flowed through the tube and separated into two components. An EDAX™ Eagle II micro x-ray fluorescence system equipped with a Rh target excitation source and a SiLi detector was used to interrogate each separated component and measure any emitted x-ray fluorescence signal. The x-ray tube of the system was operated at 40 kV and 1000 μA. The $CoK_\alpha$ and $FeK_\alpha$ x-ray emission lines were monitored to detect the $Fe^{3+}$ bound ferritin and cobalamin. The spectrum acquisition time was about 10 seconds (s). The peak due to $Fe^{3+}$ of ferritin was detected at about 9.3 min with a full-width-at-half-maximum (FWHM) of about 1.7 min. The cyanocobalamin peak was detected at about 6.3 min with FWHM of about 1 min.

The invention can be used in pharmaceutical metabolite studies to detect dangerous metabolic byproducts of a potential pharmaceutical chemical. A potential pharmaceutical chemical having at least one atom with an atomic number of nine or higher could be given to a rat (or other test animal). A blood sample would be taken from the rat before administering the potential pharmaceutical chemical to provide a baseline. After administering the potential pharmaceutical, blood from the rat would be examined for the presence of metabolites using the method of the invention.

In summary, the present invention provides an apparatus and method for detecting binding events between potential pharmaceutical chemicals and target binders. The present invention uses micro-x-ray fluorescence to determine the presence and relative amounts of elements such as fluorine, chlorine, bromine, iodine, phosphorus, and sulfur, the latter two being important constituents of enzymes, non-enzyme proteins, DNA, and RNA. Thus, the invention provides a non-destructive method of screening the binding of potential pharmaceutical chemicals with a target binder such as a protein or a nucleic acid. Known methods often require that the binder and/or potential pharmaceutical chemical include a covalently bound tag that fluoresces upon exposure to ultraviolet excitation radiation. By contrast, the invention does not require tagged materials.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practice application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for screening chemical binding, comprising:
   a flow separator configured to separate a solution of chemicals and at least one target binder into at least two flow-separated components;
   an x-ray excitation source configured to expose at least one of said flow-separated components to an x-ray excitation beam to produce an x-ray fluorescence signal therefrom, the x-ray excitation source being configured for exciting atoms of the chemical and of a chemical portion of any bound complex present in any flow-separated component;
   an x-ray detector configured to detect the x-ray fluorescence signal emitted from a flow-separated component;
   processing electronics configured to determine from the x-ray fluorescence signal produced from the excited atoms present in the chemical and the chemical portion of any bound complex present in a separated component whether or not any separated component comprises a bound complex; and
   a pump engaged with said flow separator configured to provide a pressure gradient along said flow separator.

2. The apparatus of claim 1 further comprising a diverter configured to divert a chosen flow-separated component from a remaining solution and any other flow-separated component.

3. The apparatus of claim 1 wherein said x-ray excitation beam comprises a polychromatic x-ray excitation beam.

4. The apparatus of claim 1 wherein said x-ray excitation beam comprises x-rays having an energy greater than 12 KeV.

5. The apparatus of claim 1 wherein said x-ray excitation beam comprises x-rays having an energy less than 8 KeV.

6. An apparatus for screening chemical binding, comprising:
   a flow separator configured to separate a solution into at least two flow-separated components, the solution comprising at least one chemical and at least one target binder;
   a polychromatic x-ray excitation source configured to expose at least one of the flow-separated components to a polychromatic x-ray excitation beam to produce an x-ray fluorescence signal therefrom, the polychromatic x-ray excitation source being configured for exciting atoms of the chemical and of a chemical portion of any bound complex present in any flow-separated component;
   an x-ray detector configured to detect the x-ray fluorescence signal emitted from a flow-separated component; and
   means for determining from the x-ray fluorescence signal produced from the excited atoms present in the chemical and the chemical portion of any bound complex present in a separated component whether or not any separated component comprises a bound complex.

7. The apparatus of claim 6 wherein said x-ray excitation beam comprises x-rays having an energy greater than 12 KeV.

8. The apparatus of claim 6 wherein said x-ray excitation beam comprises x-rays having an energy less then 8 KeV.

9. The apparatus of claim 6 wherein said means for determining whether or not any separated component comprises a bound complex comprises processing electronics configured to determine from the x-ray fluorescence signal produced from the excited atoms present in the chemical and the chemical portion of any bound complex present in a separated component whether or not any separated component comprises a bound complex.

10. An apparatus for screening chemical binding, comprising:
   a flow separator configured to separate a solution of chemicals and at least one target binder into at least two flow-separated components;
   an x-ray excitation source configured to expose at least one of said flow-separated components to an x-ray excitation beam comprising x-rays of less than 9 KeV to produce an x-ray fluorescence signal therefrom, the x-ray excitation source being configured for exciting atoms of the chemical and of a chemical portion of any bound complex present in any flow-separated component;
   an x-ray detector configured to detect the x-ray fluorescence signal emitted from a flow-separated component; and
   processing electronics configured to determine from the x-ray fluorescence signal produced from the excited atoms present in the chemical and the chemical portion of any bound complex present in a separated component whether or not any separated component comprises a bound complex.

* * * * *